United States Patent [19]

Eatherly et al.

[11] 4,070,514
[45] Jan. 24, 1978

[54] METHOD OF FABRICATING GRAPHITE FOR USE AS A SKELETAL PROSTHESIS AND PRODUCT THEREOF

[75] Inventors: Walter P. Eatherly; J. M. Robbins; David E. Rosson, Sr., all of Oak Ridge, Tenn.

[73] Assignee: The United States of America as represented by the United States Department of Energy, Washington, D.C.

[21] Appl. No.: 367,276

[22] Filed: June 5, 1973

[51] Int. Cl.² .............................................. A61F 1/00
[52] U.S. Cl. ............................................. 428/64; 3/1.9; 156/197; 156/296; 264/29.1; 264/29.5; 264/44; 264/317; 428/131; 428/408
[58] Field of Search ............ 264/29, 59, 44, 313, 264/317, DIG. 44, 29.1, 29.3, 29.5; 156/296, 197; 161/68; 423/447, 446; 117/46 CC; 428/64, 131, 408; 427/249

[56] References Cited
U.S. PATENT DOCUMENTS

| | | | |
|---|---|---|---|
| 3,367,812 | 2/1968 | Watts | 264/29 |
| 3,533,753 | 10/1970 | Berger | 264/44 |
| 3,539,667 | 11/1970 | Nameishi | 264/59 |
| 3,552,533 | 1/1971 | Nitz et al. | 264/29 |
| 3,825,460 | 7/1974 | Yoshikawa et al. | 264/29 |

*Primary Examiner*—Jeffery R. Thurlow
*Attorney, Agent, or Firm*—Dean E. Carlson; Stephen D. Hamel; John B. Hardaway

[57] ABSTRACT

A method for producing porous graphite for use as bone replacement with a structure for osteon penetration. Graphite is produced with ordered circular pores of 100 to 1000 microns in diameter covering at least 25% of the exposed surfaces. A cylindrical fiber is coated with a carbon flour-pitch mix and is then wound on a bobbin in a predetermined manner. The product of winding is dried, pressed, carbonized, and then graphitized. The fibers are removed either chemically or by volatilization during carbonization or graphitization.

7 Claims, 1 Drawing Figure

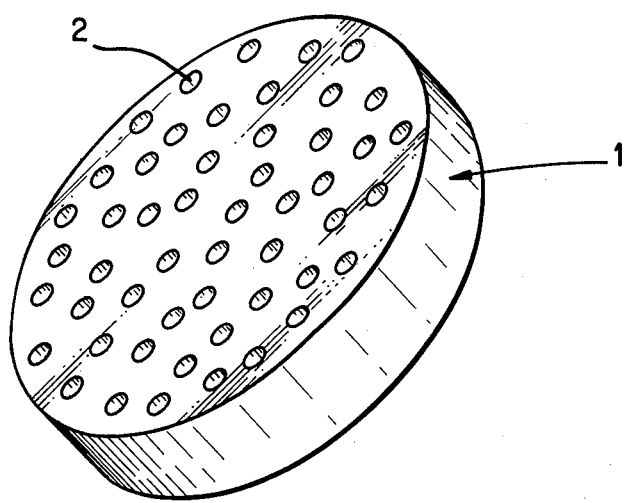

METHOD OF FABRICATING GRAPHITE FOR USE AS A SKELETAL PROSTHESIS AND PRODUCT THEREOF

This invention was made in the course of, or under, a contract with the United States Atomic Energy Commission. It relates generally to a carbon or graphite prosthetic device and to a method of producing such a device.

BACKGROUND OF THE INVENTION

Skeletal prosthesis involves two somewhat distinct problems, one of engineering the desired structure to imitate nature's functional intent, the other of developing materials commensurate with a living environment. One material believed to be suitable for use is high purity graphite. Graphite, however, has not been previously produced so as to permit bone ingrowth.

It has been previously suggested that an article containing highly oriented porosity with a pore size of 100 to 1000 microns would permit osteon penetration and thus bone ingrowth and interlocking. However, no such carbon article has previously been produced.

There are prior art methods of producing extremely porous graphites. For example, various carbon-containing organic substances have been graphitized. These include ion exchange resin beads, carbon-containing foams and the like. None of the known methods, however, provide highly oriented pores of uniform size and of circular cross section.

SUMMARY OF THE INVENTION

It is thus an object of this invention to provide a prosthetic article with controlled porosity which will permit bone ingrowth and interlocking.

It is a further object of this invention to provide a method of producing such an article.

These, as well as other objects, are accomplished by coating a fugitive fiber with a slurry of graphite precursors, arranging the fiber to create an array of parallel fibers, setting a resin binder in the slurry, removing the fibers to leave a graphite precursor relic, carbonizing and graphitizing the relic.

BRIEF DESCRIPTION OF THE DRAWING

The single FIGURE of drawing is an isometric view of a prosthetic article according to this invention.

DETAILED DESCRIPTION

According to this invention, prosthetic articles are produced with uniformly oriented pores. Such an article is shown in the single FIGURE of drawing. The article 1 comprises a section of high purity carbon and graphite with uniformly dispersed parallel pores 2 passing therethrough. In actual use such an article is implanted to directly contact the remaining bone so that the remaining bone can grow and penetrate into the pores 2. It is necessary that the pores 2 have a diameter of at least 50 micrometers, although diameters of 100 to 1000 micrometers are more desirable for such ingrowth to occur. Pore depths of from 500 to 2000 micrometers are desirable. It is preferable that the pores also cover at least 25% of the area of a cross section of the article. For a large implant, the porous prosthetic article of this invention is bonded to the ends of a larger implant so that bone ingrowth and interlocking will occur at the ends of the overall prosthetic article. The intermediate section of the overall implant is preferably made of non-porous graphite.

The purity of the graphite article is preferably greater than 99.9% so that a minimum of foreign matter is present for interaction with body tissues. The carbon and graphite material between the controlled pores preferably contains no porosity so as to maintain as high a strength as possible. However, up to 25% porosity is permissible. While the article of this invention is described as being a carbon and graphite mixture, the article may be totally carbon (i.e., amorphous carbon). However, for optimal mechanical properties, it is preferred to have 90% by volume graphite. As used within this disclosure, the term "amorphous carbon" means those forms of carbon other than graphite and diamond.

The process of this invention comprises coating a fugitive fiber with a slurry of a carbon precursor and arranging the coating fiber or fibers in a desired array with fibers parallel to one another and with the slurry filling the interstices between fibers. Preferably, the slurry contains a thermosetting binder so that the array may be isostatically pressed and heated to set the binder. However, a thermoplastic binder may also be used. After curing, the array is cut into desired sizes. The fugitive or etchable fiber may be removed at this point by chemical reaction or by vaporization during carbonization and graphitization. The cut sections are then heated from 600° to 1200° C in an inert atmosphere for 2 to 100 hours (depending on the filler-binder system used) to carbonize the section and then to 2400° to 3000° C to graphitize the carbon. Such carbonization and graphitization techniques are well known in the art.

The fugitive fiber used in the process of this invention must be one that will volatilize and leave negligible residue or be etchable at a temperature below which carbides will form. Examples of the former are nylon, acetates, and copper. Etchable fibers include monofilaments of copper, nickel, iron, tin and alloys thereof. If the carbon precursors are thermoplastic the fugitive fiber must stay in place during carbonization so as to retain the pore structure. However, if a thermosetting precursor is used the fugitive fiber need only stay in place during curing.

The carbon precursors may be any of the well-known organic or synthetic carbon-containing materials that will yield a relic carbon and/or graphite structure. Such materials include coal tar pitch, petroleum pitch, various polymers, and cokes, as examples. However, it is preferred to use a slurry of carbon and graphite powders suspended in a suitable binder (such as partially polymerized furfuryl alcohol or coal tar pitch) and a solvent such as acetone. Such a slurry may also contain graphite fibers (about 10 microns in diameter and 20 to 30 microns in length) to give added strength to the final product. The slurry tends to form a good coating material if it has a consistency about like that of molasses.

Coating is best achieved by merely passing the fiber through the slurry. It has been found helpful to vibrate the slurry during coating in order to prevent surface tension channeling around the fiber. However, any conventional coating technique, such as coextrusion, may be used. The coated fiber is best formed into a useable shape by winding so as to form an eliptical toroid having a circular cross section. After curing, sections of the toroid are cut in the form of small discs or cylinders. The winding technique is not the only method of forming an array of coated fibers. Such an array may also be formed by passing a plurality of fibers through a die while simultaneously extruding the slurry through the die so as to have a bundle of coated fibers continuously leaving the exterior of the die.

Having generally described the invention, the following specific examples are given as a further illustration thereof.

EXAMPLE I

A 0.006 inch diameter copper wire, such as is utilized for motor windings, with a polyvinyl formal resin insulating coating was passed continuously from a reel through a slurry formed from 50 g calcined air-blown coke, 30 g raw air-blown coke, and 20 g carbon black as filler and 40 g pre-polymerized furfuryl alcohol as binder combined with 4 g malaeic anhydride as a binder catalyst, and slurried with approximately 50 cc of acetone for making a molasses-like consistency. The coated wire was wound on a rotating mandrel while horizontally reciprocating the mandrel on its axis until a desired body size was attained. The resultant torus had a cross section diameter of about ⅜ inch.

After drying for 3 to 4 hours to remove any remaining acetone, the wound body was removed from the mandrel and placed in a rubber isostatic pressing bag which was then evacuated. Pressing was accomplished at 3000 psi for 16 hours at 200° C. The pressed body was cut into sections with copper fibers oriented axially, and then carbonized to 1000° C in an argon atmosphere on a 24-hour heating schedule. These pieces were subsequently graphitized at 3000° C in argon for 30 minutes. This high temperature treatment removed all visible amounts of copper. The pores were 100–150 microns in diameter and covered an estimated 30–40% of the section surface. The resultant overall density was 1.3 g/cm$^3$.

EXAMPLE II

In order to test the use of a fugitive organic fiber, short lengths of monofilament nylon of 0.006 inch diameter were mixed with a carbon flour-binder mixture similar to that described above. After pressing, the compacts were carbonized at 1000° C. This treatment removed the nylon; however, some molten nylon carbonized in and around the periphery of the pores and an optimum orientation was not achieved. Some cracking occurred due to pressure of trapped liquid nylon. A portion of these detrimental results can be overcome by the winding technique described above and controlled heating rates.

EXAMPLE III

A wound torus was prepared, dried, isostatically pressed and cut into sections by the method described in Example I. The resulting sections were carbonized in an argon atmosphere at 600° C for 4 hours. The carbonized sections were placed in a 35% aqueous nitric acid solution for 4 hours at 100° C. This removed all traces of copper leaving a carbonized relic. The relic was then heated to 3000° C for ½ hour to graphitize the carbon. The resulting sections had pores about 100 to 150 microns in diameter covering about 40% of the surface area. In using this etching technique, it appeared to be advantageous to use the copper monofilament with the polymeric coating. The coating breaks down during carbonization to leave space for the acid to attack the copper within the carbon section.

While the article of this invention has been generally described as a prosthetic device it is readily apparent that other utilities inhere in such an article. Such other utilities may include use as an essentially inert filter or sieve, or if activated, as a catalyst or catalyst support.

What is claimed is:

1. A method for producing a prosthetic article, comprising the steps of:
   passing a fugitive fiber through a slurry comprising a carbon powder filler and a thermosetting carbon precursor binder to coat said fiber with said slurry;
   winding said fiber into a generally elliptical toroidal configuration having cross sections containing a parallel array of fibers created by the arrangement of said fugitive fiber, said parallel array of fibers having interstices between said fibers substantially filled with said slurry;
   setting said binder to create a cured configuration;
   cutting said cured configuration at points substantially perpendicular to said parallel array to produce a plurality of generally cylindrical sections having said parallel array of fibers embodied therein with said fibers being substantially parallel to the axis of each said cylindrical section;
   destructively removing said parallel array of fibers from said cylindrical sections to leave uniformly dispersed generally parallel pores having a diameter within the range of 100 to 1000 micrometers within carbon precursor relics; and
   carbonizing said relics.

2. The method according to claim 1 further including graphitizing said relic.

3. The method according to claim 1 wherein said step of removing comprises volatilizing said fiber by heating.

4. The method according to claim 1 wherein said step of removing comprises etching said fiber.

5. The method according to claim 1 wherein said fiber is selected from the group consisting of nylon, copper, tin, and iron.

6. The method according to claim 1 wherein said carbon powder comprises raw air-blown coke, calcined air-blown coke, and carbon black, said binder is selected from the group consisting of pre-polymerized furfuryl alcohol and coal tar pitch and said slurry further comprises acetone as a solvent.

7. The product produced by the process of claim 1.

* * * * *